US009179980B2

(12) United States Patent
Yoon

(10) Patent No.: US 9,179,980 B2
(45) Date of Patent: Nov. 10, 2015

(54) SURGICAL ROBOT SYSTEM FOR PERFORMING SURGERY BASED ON DISPLACEMENT INFORMATION DETERMINED BY THE SPECIFICATION OF THE USER, AND METHOD FOR CONTROLLING SAME

(75) Inventor: Sang Jin Yoon, Seoul (KR)

(73) Assignee: RIMSCIENCE CO., LTD., Seoul (KR)

( * ) Notice: Subject to any disclaimer, the term of this patent is extended or adjusted under 35 U.S.C. 154(b) by 104 days.

(21) Appl. No.: 14/000,827

(22) PCT Filed: Jan. 31, 2012

(86) PCT No.: PCT/KR2012/000767
§ 371 (c)(1),
(2), (4) Date: Aug. 21, 2013

(87) PCT Pub. No.: WO2012/115360
PCT Pub. Date: Aug. 30, 2012

(65) Prior Publication Data
US 2013/0331861 A1    Dec. 12, 2013

(30) Foreign Application Priority Data
Feb. 21, 2011    (KR) ........................ 10-2011-0015251

(51) Int. Cl.
*A61B 19/00* (2006.01)
*A61B 1/00* (2006.01)
*A61B 17/29* (2006.01)

(52) U.S. Cl.
CPC ......... *A61B 19/2203* (2013.01); *A61B 1/00133* (2013.01); *A61B 1/00149* (2013.01); *A61B 2017/2906* (2013.01); *A61B 2019/2211* (2013.01); *A61B 2019/462* (2013.01); *A61B2019/5217* (2013.01); *A61B 2019/5265* (2013.01); *G05B 2219/40418* (2013.01)

(58) Field of Classification Search
CPC ........... A61B 1/00133; A61B 1/00149; A61B 19/2203; A61B 2017/2906; A61B 2019/2211; A61B 2019/462; A61B 2019/5217; A61B 2019/5265; G05B 2219/40418
USPC ................... 700/250, 251, 257, 259; 606/130
See application file for complete search history.

(56) References Cited

U.S. PATENT DOCUMENTS

| 8,760,391 B2 * | 6/2014 | Hawkins ........................ 345/156 |
| 8,830,224 B2 * | 9/2014 | Zhao et al. .................... 345/419 |
| 8,888,782 B2 * | 11/2014 | Smith et al. ..................... 606/81 |

(Continued)

FOREIGN PATENT DOCUMENTS

| KR | 10-20100098055 A | 9/2010 |
| KR | 10-20100112310 A | 10/2010 |

(Continued)

OTHER PUBLICATIONS

International Search Report for PCT Application No. PCT/KR2012/000767, dated Sep. 25, 2012.

*Primary Examiner* — Jason Holloway
(74) *Attorney, Agent, or Firm* — Mayer Brown LLP; Hyunho Park

(57) ABSTRACT

There is provided a surgical robot system comprising a robot, a control system and a user control device, wherein the robot comprises an endoscope and at least one surgical instrument; the user control device comprises a display means by which a user may make an indication on an internal body part; and the control system comprises a displacement information processing unit and a surgical instrument control unit.

25 Claims, 6 Drawing Sheets

(56) References Cited

U.S. PATENT DOCUMENTS

| | | | |
|---|---|---|---|
| 2006/0258938 A1* | 11/2006 | Hoffman et al. | 600/424 |
| 2010/0013766 A1* | 1/2010 | Gu et al. | 345/158 |
| 2010/0164950 A1* | 7/2010 | Zhao et al. | 345/419 |
| 2010/0166323 A1* | 7/2010 | Zhao et al. | 382/218 |
| 2014/0300722 A1* | 10/2014 | Garcia | 348/77 |

FOREIGN PATENT DOCUMENTS

| | | |
|---|---|---|
| KR | 10-0997194 B1 | 11/2010 |
| KR | 10-2011-0004496 B1 | 1/2011 |

* cited by examiner

SURGICAL ROBOT SYSTEM FOR PERFORMING SURGERY BASED ON DISPLACEMENT INFORMATION DETERMINED BY THE SPECIFICATION OF THE USER, AND METHOD FOR CONTROLLING SAME

FIELD OF THE INVENTION

The present invention relates to a surgical robot system for performing surgery based on displacement information determined by user indication and a method for controlling the same.

BACKGROUND

Traditionally, surgery has been only performed by trained surgeons. However, with the gradual development of surgical robot systems, surgeons are now handing over some areas of surgery to the surgical robot systems. One representative example of such surgical robot systems is the da Vinci™ Surgical System from Intuitive Surgical, Inc. of the Unites States. However, even with the da Vinci system, which is one of the most advanced surgical robot systems, surgery can only be performed when a surgeon who received special manipulation training controls the actions of surgical instruments individually by manipulating the handle, stick, foot board or the like of the system while watching the monitor. Therefore, it is difficult to say that there exist fully-intelligent surgical robot systems at present.

In this regard, the inventor has devised a surgical robot system and a method for controlling the same, wherein surgery can be performed so that the actions of surgical instruments are intelligently controlled based on the indications made by a user such as a surgeon according to the user's intuition.

SUMMARY OF THE INVENTION

The present invention is to resolve all of the above-described prior art issues.

It is an objective of the present invention to provide a surgical robot system and a method for controlling the same, wherein surgery can be performed so that the actions of surgical instruments are intelligently controlled based on the indications made by a user according to the user's intuition.

It is another objective of the present invention to provide an intelligent surgical robot system and a method for controlling the same, wherein the user's convenience is maximized and the user's manipulation is minimally required.

It is yet another objective of the present invention to provide a surgical robot system and a method for controlling the same, wherein surgery can be performed accurately, rapidly and easily.

The representative aspects of the present invention to achieve the above objectives are described below.

According to one aspect of the present invention, there is provided a surgical robot system comprising a robot, a control system and a user control device, wherein the robot comprises an endoscope and at least one surgical instrument; the user control device comprises a display means by which a user may make an indication on an internal body part; and the control system comprises a displacement information processing unit for determining displacement information according to reference coordinates of the robot, based on information on the displacement of lines or outlines in the display means according to the user's indication in the display means, and the distance between the endoscope and the internal body part observed by the endoscope; and a surgical instrument control unit for controlling the surgical instrument of the robot to be relocated or perform predetermined surgical actions, based on the displacement information according to the reference coordinates of the robot.

According to one aspect of the present invention, there is provided a method for controlling a surgical robot system comprising a robot and a user control device, the robot comprising an endoscope and at least one surgical instrument, the user control device comprising a display means by which a user may make an indication on an internal body part, and the method comprising the steps of: determining displacement information according to reference coordinates of the robot, based on information on the displacement of lines or outlines in the display means according to the user's indication in the display means, and the distance between the endoscope and the internal body part observed by the endoscope; and controlling the surgical instrument of the robot to be relocated or perform predetermined surgical actions, based on the displacement information according to the reference coordinates of the robot.

In addition, another system or method to implement the present invention is further provided.

According to the present invention, there is provided a surgical robot system and a method for controlling the same, wherein surgery can be performed so that the actions of surgical instruments are intelligently controlled based on the indications made by a user according to the user's intuition.

According to the present invention, there is provided an intelligent surgical robot system and a method for controlling the same, wherein the user's convenience is maximized and the user's manipulation is minimally required.

According to the present invention, there is provided a surgical robot system and a method for controlling the same, wherein surgery can be performed accurately, rapidly and easily.

DETAILED DESCRIPTION OF THE INVENTION

Figure 1:
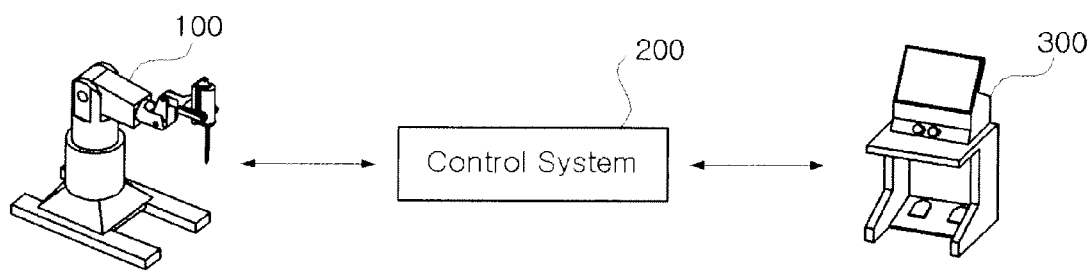
FIG. 1 is a schematic diagram of the entire structure of a surgical robot system according to one embodiment of the present invention.

In the following detailed description of the present invention, reference is made to the accompanying drawings that show, by way of illustration, specific embodiments in which the present invention may be practiced. These embodiments are described in sufficient detail to enable those skilled in the art to practice the present invention. It is to be understood that the various embodiments of the invention, although different, are not necessarily mutually exclusive. For example, a particular feature, structure, or characteristic described herein, in connection with one embodiment, may be implemented within other embodiments without departing from the spirit and scope of the present invention. In addition, it is to be understood that the location or arrangement of individual elements within each disclosed embodiment may be modified without departing from the spirit and scope of the present invention. The following detailed description is, therefore, not to be taken in a limiting sense, and the scope of the present invention encompasses the entire subject matter covered by the appended claims and the full range of equivalents to which the claims are entitled. In the drawings, like reference numerals refer to the same or similar elements throughout the several views.

Hereinafter, various preferred embodiments of the present invention will be described below in detail with reference to the accompanying drawings such that those skilled in the art to which the present invention pertains can easily practice the present invention.

PREFERRED EMBODIMENTS OF THE INVENTION

Structure of the Entire System

Figure 2:
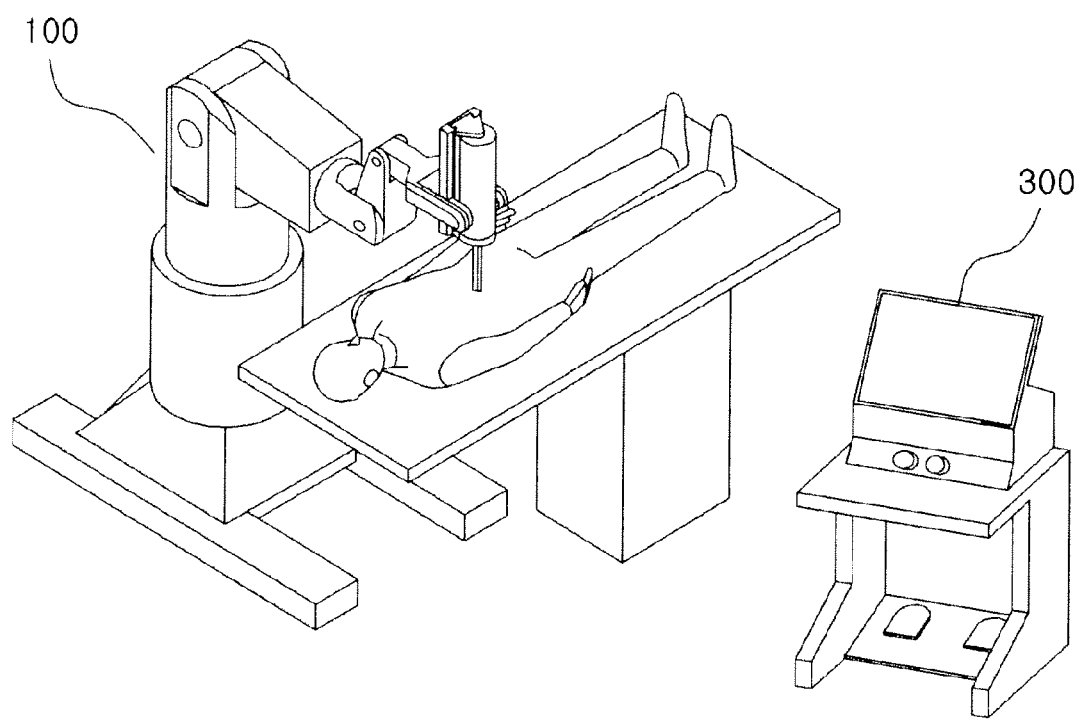
FIG. 2 shows a situation before a user actually performs surgery using the surgical robot system.

FIG. 1 is a schematic diagram of the entire structure of a surgical robot system according to one embodiment of the present invention. As shown in FIG. 1, the surgical robot system may comprise a robot (or an operation robot) 100, a control system 200 and a user control device 300. FIG. 2 shows a situation before a user actually performs surgery using the surgical robot system.

First, the robot 100 according to one embodiment of the invention may be a mechanical device which comprises a base, a plurality of robotic arms, an endoscope, at least one surgical instrument and the like to perform surgery according to the control of the control system 200. In particular, a distance measurement module (not shown) such as an ultrasonic distance meter may be provided at the end (or elsewhere) of the endoscope of the robot 100. Data or information determined in the distance measurement module may be used in the control system 200 as described below. The robot 100 may be implemented without limitation as desired by those skilled in the art, as long as it falls within the spirit of the present invention. Examples of the detailed structure of the robot 100 can be found in the specification of Korean Patent Application No. 2008-108103, the entire content of which is incorporated herein by reference.

Next, the control system 200 according to one embodiment of the invention may be a computer system to determine displacement information according to reference coordinates of the robot 100, based on information on the indication made by the user in the display means of the user control device 300 and the distance between the endoscope of the robot 100 and the internal body part observed by the endoscope, and to control the action of the corresponding surgical instrument of the robot 100 based on the displacement information. Examples of the detailed structure of the control system 200 will be described below with reference to FIG. 3.

Lastly, the user control device 300 according to one embodiment of the invention may be a control device which comprises a display means, a user indication means, a user command means and the like to allow a user to make an indication or issue a command for a relocated surgical instrument.

The display means of the user control device 300 may function to display to the user the internal body part observed by the endoscope of the robot 100 with a predetermined magnification and transmit to the control system 200 the information on the displacement of lines or outlines in the display means, which is determined by the user's indication. To this end, the display means may comprise a display panel for two-dimensional display or a display space (not shown) for three-dimensional display, and a processor (not shown) which may be combined with the display panel or display space to determine the information on the displacement of lines or outlines in the display panel or display space according to the user's indication. Herein, the display panel may be a known two-dimensional display device such as an LCD panel, a PDP panel and an LED display device which can display visual representations in two dimensions, and the display space may be a known three-dimensional display device such as a holographic display device. Examples of the above processor include a known processor for a touch panel or a known processor for three-dimensional location recognition. Meanwhile, instead of the above display space, a model made in imitation of a specific internal body part or organ (e.g., a model equipped with an electronic responsive means thereon) may be employed.

Figure 5:
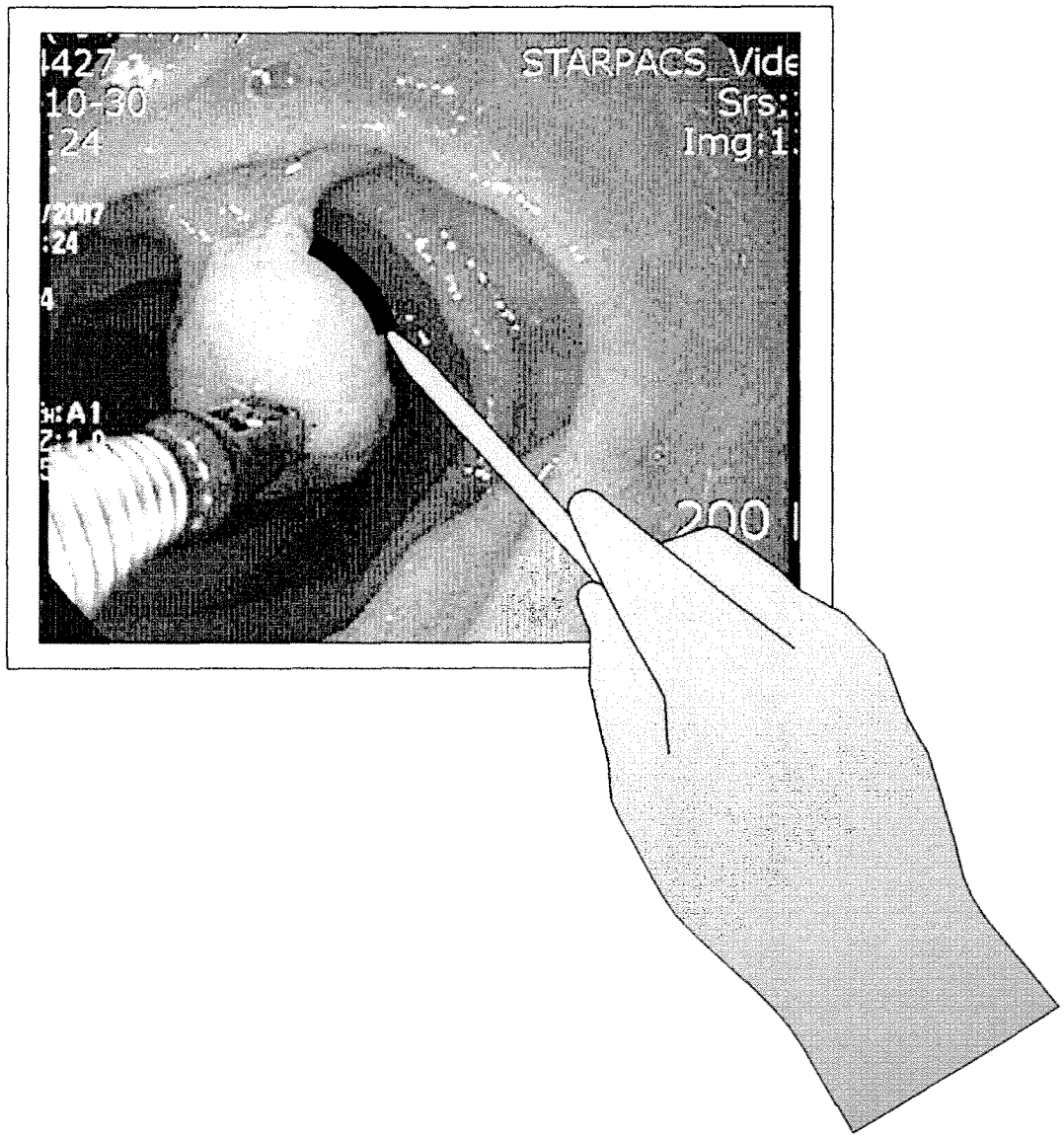
FIG. 5 illustrates that a user has made an indication on an internal body part on the display panel according to one embodiment of the present invention.
Figure 6:
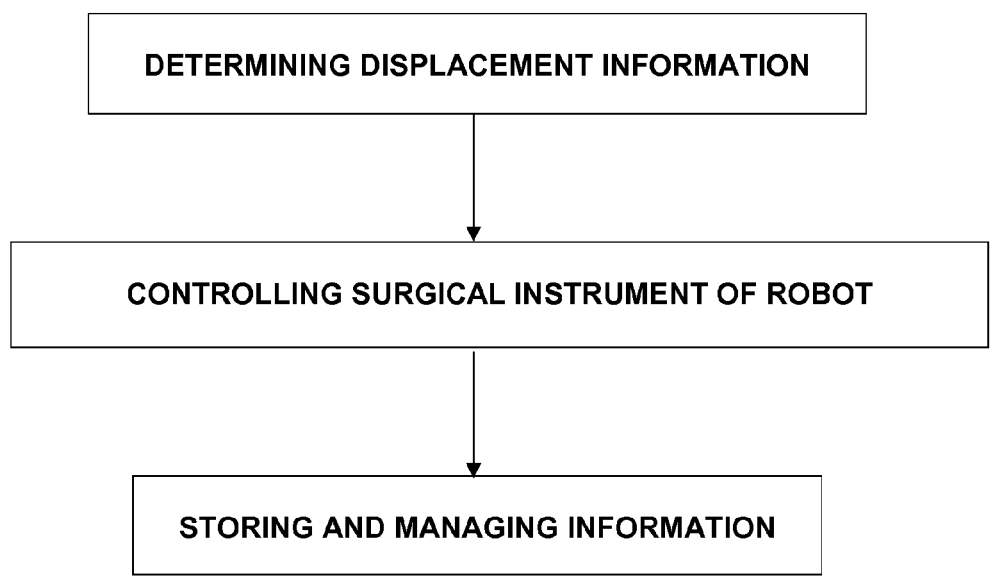
FIG. 6 illustrates a flow chart for a process for controlling a surgical robot system according to one embodiment of the present invention.

FIG. 5 illustrates that a user has made an indication on an internal body part on the display panel according to one embodiment of the present invention. Referring to FIG. 5 as well as the above description facilitates understanding of the user's indication in the display means.

The user indication means of the user control device 300 may function to allow the user's indication to be recognized by the display means when the user holds the user indication means and makes the indication in the display means. Examples of the user indication means include a variety of known tools such as a mouse, an electronic pen, a light pen and a trackball.

The user command means of the user control device 300 may be various types of command means to allow the user to select the desired surgical instrument or command the surgical instrument to relocate as per the user's indication and then perform surgical actions such as holding, fastening, searing, incising, and suturing of the internal body part indicated by the user. The user command means may be implemented in the form of a control panel or control buttons separately from the display means, but may also be configured in combination with the display means. For example, if the display means is a touch panel, then the user command means may be the window or graphical buttons of the touch panel.

Structure of the Control System

Figure 3:
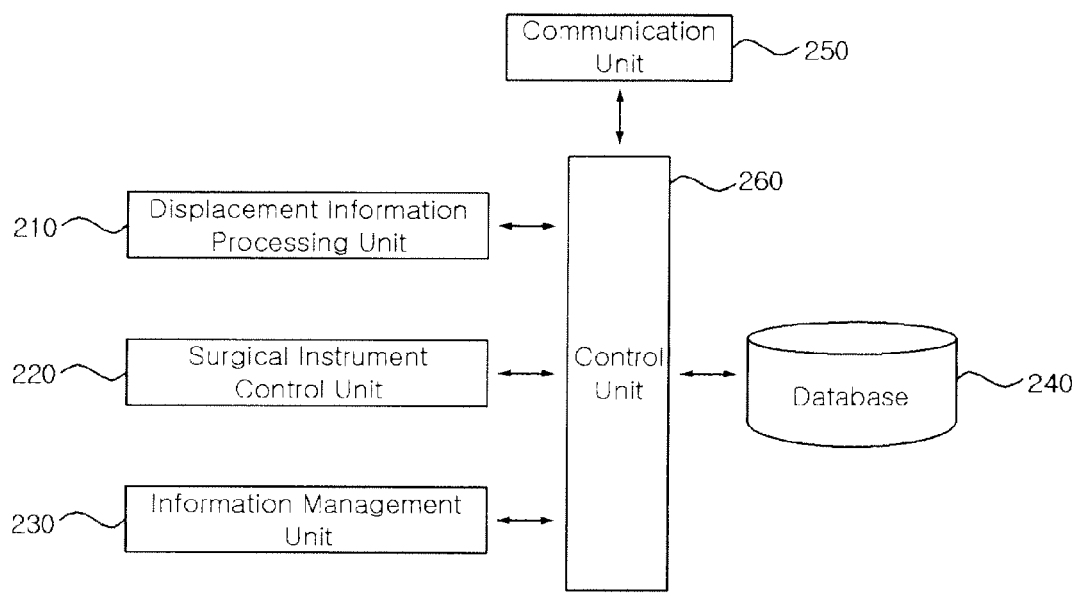
FIG. 3 is a detailed diagram of the internal structure of a control system according to one embodiment of the present invention.

FIG. 3 is a detailed diagram of the internal structure of the control system 200 according to one embodiment of the present invention.

As shown in FIG. 3, the control system 200 according to one embodiment of the invention may comprise a displacement information processing unit 210, a surgical instrument control unit 220, an information management unit 230, a database 240, a communication unit 250, and a control unit 260. According to one embodiment of the invention, at least some of the displacement information processing unit 210, the surgical instrument control unit 220, the information management unit 230, the database 240, the communication unit 250, and the control unit 260 may be program modules that communicate with the robot 100 or the user control device 300. Such program modules may be included in the control system 200 in the form of operating systems, application modules or other program modules, and may be physically stored in a variety of known storage devices. Further, such program modules may be stored in a remote storage device capable of communicating with the control system 200. The program modules include, but are not limited to, routines, subroutines, programs, objects, components, data structures and the like to perform specific tasks or implement specific abstract data types according to the present invention, which are to be described below.

Meanwhile, the control system 200 may be separated from or physically combined with the robot 100 and/or the user control device 300, as desired by those skilled in the art.

The displacement information processing unit 210 according to one embodiment of the invention may operate to determine displacement information according to reference coordinates of the robot 100, when the user makes an indication in the display means of the user control device 300, based on the information on the user's indication in the display means and the distance between the endoscope of the robot 100 and the internal body part observed by the endoscope. The above operation may be performed in the following steps.

1. Receiving the Information on the Displacement of Lines or Outlines in the Display Means According to the User's Indication The displacement information processing unit 210 may receive from the display means the information on the displacement of lines or outlines in the display means (e.g., the origin of the displacement being at the center of the display means) according to the user's indication. The information on the displacement may be a set of a plurality of two-dimensional or three-dimensional displacement vectors. This set will be denoted as D' below (In the following description, capital letters denote vectors and small letters denote scalar values in general).

2. Determining the Distance Between the Endoscope of the Robot 100 and the Internal Body Part Observed by the Endoscope The displacement information processing unit 210 may receive from the robot 100 the raw data on the distance between the endoscope of the robot 100 and the internal body part observed by the endoscope (e.g., turnaround time of ultrasonic waves) or the information on the distance itself, thereby determining the distance d.

3. Determining the Displacement Information According to Reference Coordinates of the Robot 100

The displacement information processing unit 210 may determine the displacement information according to the reference coordinates of the robot 100 (e.g., the origin of the coordinates being at the observation location of the endoscope of the robot 100), which corresponds to the displacement of lines or outlines in the display means according to the user's indication. The displacement information may also be a set of a plurality of two-dimensional or three-dimensional displacement vectors. This set will be denoted as D below.

In this case, the following equation may be obtained.

$$D=F(d) \times D' \quad \text{(Eq. 1)}$$

Herein, F(d) is a vector function which is determined by d and approximately converts D' into D as appropriate. F(d) may be an empirical formula that may be determined from appropriate trials or a simple magnification determination formula that is determined based on the magnification of the endoscope.

Meanwhile, if F is confirmed through a sufficient number of trials, then Eq. 1 may be changed as below.

$$D=F(d,D') \quad \text{(Eq. 2)}$$

That is, F is not merely a vector function for approximate conversion, but may also be a vector function to convert D' into D (nearly) exactly.

Therefore, the displacement information processing unit 210 may determine D, the displacement information according to the reference coordinates of the robot 100.

Meanwhile, when the user indication is changed by the user, the displacement information processing unit 210 may modify the previously determined displacement information according to the reference coordinates of the robot 100. That is, when the user observes in the display means that the surgical instrument has been actually relocated to the internal body part by the action of the surgical instrument control unit 220 to be described below, and then changes the previous user indication in the display means (e.g., redraws the outlines that the user has indicated), the displacement information processing unit 210 may modify the displacement information according to the reference coordinates of the robot 100 based on the changed user indication.

Next, the surgical instrument control unit 220 according to one embodiment of the invention may control the corresponding surgical instrument of the robot 100 to be actually relocated or control the relocated surgical instrument to perform predetermined surgical actions, based on the displacement information according to the reference coordinates of the robot 100 determined in the displacement information processing unit 210.

First, the surgical instrument control unit 220 may determine the information on the displacement to be eventually taken by the surgical instrument of the robot 100 (i.e., the set of displacement vectors to be taken by the end effector of the surgical instrument that actually performs the surgical actions) so that the surgical instrument is relocated according to the user indication. Hereinafter, it will be denoted as Dt.

In the above case, the following equation may be obtained.

$$Dt=D-Rt \quad \text{(Eq. 3)}$$

Herein, Rt is a vector that represents the default displacement of the surgical instrument with respect to the reference coordinates of the robot 100. Rt may also be a vector that is predetermined for each surgical instrument.

Figure 4:
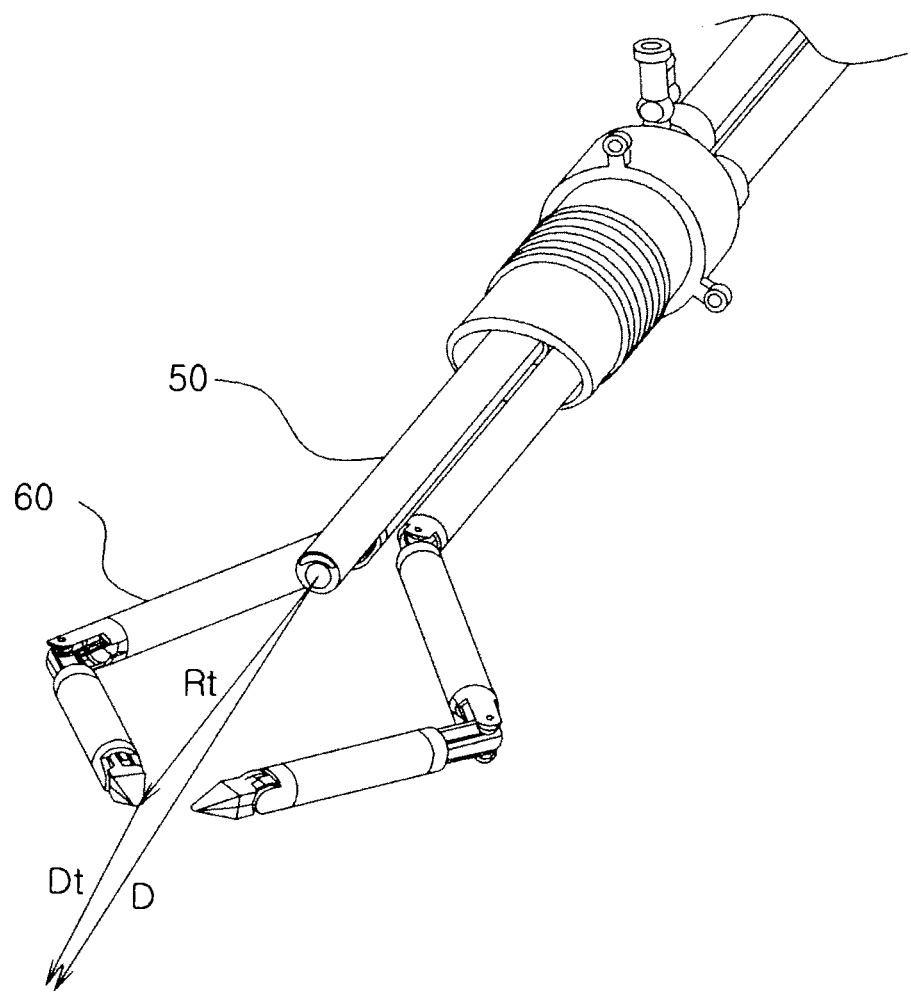
FIG. 4 illustrates that the endoscope and surgical instrument of the robot are positioned together according to one embodiment of the present invention.

This will be further discussed with reference to FIG. 4. FIG. 4 illustrates that the endoscope 50 and the surgical instrument 60 of the robot 100 are positioned together according to one embodiment of the present invention. For example, if the coordinate reference of the robot 100 is at the end of the endoscope 50, then the end effector of the surgical instrument 60 may be relocated by Dt as illustrated.

Further, the surgical instrument control unit 220 may allow the surgical instrument to be selected as per the commands issued by the user in the user command means, or control the surgical instrument to be relocated by Dt and perform the surgical actions as per the commands issued by the user in the user command means. Examples of the possible surgical actions according to the type of the end effector of the surgical instrument are as described above.

Next, the information management unit 230 according to one embodiment of the invention may store and manage the information on the indications or commands made by an experienced user according to the type, profile, size, name of the related disease, stage of the related disease or the like of the internal body part on which the surgery has been carried out by the surgical robot system. Such information may be stored in the database 240 together with the images of the corresponding internal body part before the surgery.

Therefore, the user may first photograph the corresponding internal body part before the surgery and then use the photographed images, specifying the type or the like of the corresponding internal body part in some cases, to search the similar images from the database 240. Since the searched images are stored together with the information on the indications or commands made by previous users, the user may consult the information or utilize it as it is, thereby performing the surgery more accurately, rapidly and easily.

Next, the database 240 according to one embodiment of the invention may store the information on the indications or commands made by the user in the process of performing the surgery as described above. Although FIG. 3 shows that the database 240 is configured to belong to the control system 200, the database 240 may be configured separately from the control system 200, as needed by those skilled in the art to implement the present invention. For example, the database 240 may be built on a web server (not shown) so that it may be consulted by a large number of distributed users.

Next, the communication unit 250 according to one embodiment of the invention may function to enable data reception and transmission from/to the displacement information processing unit 210, the surgical instrument control unit 220, the information management unit 230, and the database 240.

Lastly, the control unit 260 according to one embodiment of the invention may function to control data flow among the displacement information processing unit 210, the surgical instrument control unit 220, the information management unit 230, the database 240, and the communication unit 250. That is, the control unit 260 according to the present invention may control data flow into/out of the control system 200 or data flow among the components of the control system 200, such that the displacement information processing unit 210, the surgical instrument control unit 220, the information management unit 230, the database 240, and the communication unit 250 may carry out their particular functions, respectively.

The embodiments according to the present invention as described above may be implemented in the form of program instructions that can be executed by various computer components, and may be stored on a computer-readable recording medium. The computer-readable recording medium may include program instructions, data files, data structures and the like separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be changed to one or more software modules to perform the operations of the present invention, and vice versa.

Although the present invention has been described above in connection with specific limitations such as detailed components as well as limited embodiments and drawings, these are merely provided to aid general understanding of the invention. The present invention is not limited to the above embodiments, and those skilled in the art will appreciate that various changes and modifications are possible from the above description.

Therefore, the spirit and scope of the present invention is not to be limited by the above-described embodiments, but rather is to be defined by the accompanying claims and equivalents thereof.

What is claimed is:

1. A surgical robot system, comprising:
   a robot;
   a control system; and
   a user control device,
   wherein the robot comprises an endoscope and at least one surgical instrument;
   the user control device comprises a display means by which a user makes an indication on an internal body part; and
   the control system comprises:
   a displacement information processing unit configured to determine displacement information according to reference coordinates of the robot, based on information on the displacement of lines or outlines in the display means according to the user's indication in the display means, and the distance between the endoscope and the internal body part observed by the endoscope; and
   a surgical instrument control unit configured to control the surgical instrument of the robot to be relocated or perform predetermined surgical actions, based on the displacement information according to the reference coordinates of the robot.

2. The surgical robot system of claim 1, wherein the endoscope comprises a distance measurement module.

3. The surgical robot system of claim 2, wherein the distance measurement module is provided at the end of the endoscope.

4. The surgical robot system of claim 1, wherein the display means is a display panel for two-dimensional display or a display space for three-dimensional display.

5. The surgical robot system of claim 1, wherein the displacement information according to the reference coordinates of the robot (D) is determined by the following equation:

$$D = F(d) \times D' \qquad (\text{Eq. 1})$$

wherein d is the distance and D' is the information on the displacement according to the user's indication in the display means.

6. The surgical robot system of claim 1, wherein the displacement information according to the reference coordinates of the robot (D) is determined by the following equation:

$$D = F(d, D') \qquad (\text{Eq. 2})$$

wherein d is the distance and D' is the information on the displacement according to the user's indication in the display means.

7. The surgical robot system of claim 1, wherein the user's indication may be modified by the user on the display means.

8. The surgical robot system of claim 1, wherein the surgical instrument control unit determines information on the displacement to be taken by the surgical instrument.

9. The surgical robot system of claim 8, wherein the information on the displacement to be taken by the surgical instrument is a set of displacement vectors to be taken by an end effector of the surgical instrument.

10. The surgical robot system of claim 1, wherein the surgical instrument control unit controls the surgical instrument to be relocated and perform the surgical actions as per the user's commands.

11. The surgical robot system of claim 10, wherein the surgical actions are at least one of holding, fastening, searing, incising, and suturing.

12. The surgical robot system of claim 1, wherein the control system further comprises an information management unit, and the information management unit stores and manages, in a database, information on the indications or commands made by previous users according to the type, profile, size, name of the related disease, or stage of the related disease of the internal body part on which the surgery has been previously carried out.

13. The surgical robot system of claim 12, wherein the information management unit further stores and manages, in the database, images of the internal body part on which the surgery has been previously carried out.

14. The surgical robot system of claim 13, wherein the images may be image-searched from the database.

15. A method for controlling a surgical robot system comprising a robot and a user control device, the robot comprising an endoscope and at least one surgical instrument, the user control device comprising a display means by which a user makes an indication on an internal body part, and the method comprising the steps of:
 determining displacement information according to reference coordinates of the robot, based on information on the displacement of lines or outlines in the display means according to the user's indication in the display means, and the distance between the endoscope and the internal body part observed by the endoscope; and
 controlling the surgical instrument of the robot to be relocated or perform predetermined surgical actions, based on the displacement information according to the reference coordinates of the robot.

16. The method of claim 15, wherein the displacement information according to the reference coordinates of the robot (D) is determined by the following equation:

$$D = F(d) \times D' \qquad \text{(Eq. 1)}$$

wherein d is the distance and D' is the information on the displacement according to the user's indication in the display means.

17. The method of claim 15, wherein the displacement information according to the reference coordinates of the robot (D) is determined by the following equation:

$$D = F(d, D') \qquad \text{(Eq. 2)}$$

wherein d is the distance and D' is the information on the displacement according to the user's indication in the display means.

18. The method of claim 15, wherein the user's indication may be modified by the user on the display means.

19. The method of claim 15, further comprising the step of determining information on the displacement to be taken by the surgical instrument.

20. The method of claim 19, wherein the information on the displacement to be taken by the surgical instrument is a set of displacement vectors to be taken by an end effector of the surgical instrument.

21. The method of claim 15, further comprising the step of controlling the surgical instrument to be relocated and perform the surgical actions as per the user's commands.

22. The method of claim 21, wherein the surgical actions are at least one of holding, fastening, searing, incising, and suturing.

23. The method of claim 15, further comprising the step of storing and managing, in a database, information on the indications or commands made by previous users according to the type, profile, size, name of the related disease, or stage of the related disease of the internal body part on which the surgery has been previously carried out.

24. The method of claim 23, wherein the database further stores and manages images of the internal body part on which the surgery has been previously carried out.

25. The method of claim 24, wherein the images may be image-searched from the database.

* * * * *